US010060939B2

(12) United States Patent
Rosenbloom

(10) Patent No.: US 10,060,939 B2
(45) Date of Patent: Aug. 28, 2018

(54) DEVICE AND METHOD FOR CLINICAL DATA SAMPLING AND SPECIMEN BANKING

(71) Applicant: CARNEGIE MELLON UNIVERSITY, a Pennsylvania Non-Profit Corporation, Pittsburgh, PA (US)

(72) Inventor: Alan Rosenbloom, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 14 days.

(21) Appl. No.: 15/114,933

(22) PCT Filed: Jan. 30, 2015

(86) PCT No.: PCT/US2015/013859
§ 371 (c)(1),
(2) Date: Jul. 28, 2016

(87) PCT Pub. No.: WO2015/116978
PCT Pub. Date: Aug. 6, 2015

(65) Prior Publication Data
US 2016/0341754 A1    Nov. 24, 2016

Related U.S. Application Data

(60) Provisional application No. 61/965,488, filed on Jan. 31, 2014, provisional application No. 61/996,430, filed on May 7, 2014.

(51) Int. Cl.
*G01N 35/08* (2006.01)
*G01N 1/18* (2006.01)
(Continued)

(52) U.S. Cl.
CPC ........... *G01N 35/085* (2013.01); *A61B 5/155* (2013.01); *A61B 5/150229* (2013.01);
(Continued)

(58) Field of Classification Search
CPC ................................. G01N 35/08; G01N 1/18
(Continued)

(56) References Cited

U.S. PATENT DOCUMENTS 3,480,369 A * 11/1969 Smythe ................. G01N 21/05
346/33 A
5,268,147 A * 12/1993 Zabetakis ........... B01F 13/0809
422/68.1
(Continued)

OTHER PUBLICATIONS

International Search Report and Written Opinion of the International Searching Authority for PCT Application PCT/US2015/013859 dated Apr. 17, 2015.
(Continued)

*Primary Examiner* — Arlen Soderquist
(74) *Attorney, Agent, or Firm* — Michael G. Monyok; David G. Oberdick

(57) ABSTRACT

A system and method are described that allow the autonomous collection of relevant data and samples from a patient during a clinical trial or during routine care. Sampling is accomplished by drawing multiple samples into tubing, such as microfluidic tubing, and using a pump to move the samples through the tubing. A spacer fluid is provided to separate each sample and to prevent contamination between each. A microcontroller is used to control the operation of the pump and to gather data about the patient from the electronic medical record or other alternative inputs, and the sampling, including data from onboard sensors.

22 Claims, 5 Drawing Sheets

(51) Int. Cl.
  *A61B 10/00* (2006.01)
  *A61B 5/15* (2006.01)
  *A61B 5/155* (2006.01)
  *G01N 33/546* (2006.01)
  *G01N 1/10* (2006.01)
  *G06F 19/00* (2018.01)
  *H04B 1/40* (2015.01)

(52) U.S. Cl.
  CPC ...... *A61B 5/150946* (2013.01); *A61B 10/007* (2013.01); *G01N 1/18* (2013.01); *G01N 33/546* (2013.01); *G01N 2001/1031* (2013.01); *G06F 19/322* (2013.01); *H04B 1/40* (2013.01)

(58) Field of Classification Search
  USPC ...................................... 422/82; 436/53, 180
  See application file for complete search history.

(56) References Cited

U.S. PATENT DOCUMENTS

| | | | |
|---|---|---|---|
| 5,573,651 A | 11/1996 | Dasgupta | |
| 5,640,954 A | 6/1997 | Pfeiffer et al. | |
| 6,348,354 B1* | 2/2002 | Adolfsen | G01N 35/08 422/105 |
| 6,623,971 B2* | 9/2003 | Adolfsen | G01N 35/0095 422/105 |
| 7,142,987 B2* | 11/2006 | Eggers | B01L 3/5085 702/19 |
| 8,420,397 B2* | 4/2013 | Joanicot | B01L 3/502738 422/402 |
| 2003/0082081 A1* | 5/2003 | Fouillet | B01F 13/0071 506/33 |
| 2003/0235919 A1 | 12/2003 | Chandler | |
| 2004/0168934 A1 | 9/2004 | Schaupp et al. | |
| 2005/0272159 A1 | 12/2005 | Ismagilov | |
| 2005/0276728 A1* | 12/2005 | Muller-Cohn | A01N 1/00 422/400 |
| 2006/0094119 A1* | 5/2006 | Ismagilov | B01F 13/0071 436/55 |
| 2007/0117212 A1 | 5/2007 | Kautz et al. | |
| 2007/0292310 A1 | 12/2007 | Gravesen | |
| 2010/0022414 A1 | 1/2010 | Link | |
| 2010/0179397 A1 | 7/2010 | Bright | |
| 2011/0311978 A1 | 12/2011 | Makarewicz | |
| 2012/0016216 A1* | 1/2012 | Subrebost | A61B 5/14525 600/316 |
| 2012/0122714 A1 | 5/2012 | Samuels | |
| 2012/0302448 A1 | 11/2012 | Hutchison | |
| 2012/0309297 A1* | 12/2012 | Bates | G11B 5/00821 455/39 |

OTHER PUBLICATIONS

Kovarik, Michelle L. et al. "Micro total analysis systems: fundamental advances and applications in the laboratory, clinic, and field." Analytical chemistry 85, No. 2 (2012): 451-472.

Li, Liang et al. "Nanoliter microfluidic hybrid method for simultaneous screening and optimization validated with crystallization of membrane proteins." Proceedings of the National Academy of Sciences 103, No. 51 (2006): 19243-19248.

Chan, Marie et al. "Smart wearable systems: Current status and future challenges." Artificial intelligence in medicine 56, No. 3 (2012): 137-156.

Venugopal, Manju et al. "Clinical evaluation of a novel interstitial fluid sensor system for remote continuous alcohol monitoring." IEEE Sensors Journal 8, No. 1 (2008): 71-80.

European Search Report for European Application 15744076.9 dated Sep. 21, 2017.

* cited by examiner

DEVICE AND METHOD FOR CLINICAL DATA SAMPLING AND SPECIMEN BANKING

CROSS-REFERENCE TO RELATED APPLICATIONS

This application claims the benefit under 35 U.S.C. § 119 of U.S. Provisional Application Ser. No. 61/965,488, filed Jan. 31, 2014, and U.S. Provisional Application Ser. No. 61/996,430, filed May 7, 2014, both of which are incorporated by reference herein in their entirety.

STATEMENT REGARDING FEDERALLY SPONSORED RESEARCH

Not Applicable.

BACKGROUND OF THE INVENTION

The invention relates generally to the field of sampling and storing specimens collected from a patient, which can occur in the setting of a clinical trial or routine patient care. Medicine is becoming increasingly personalized, where molecular markers of disease (biomarkers) promise to detect conditions earlier and with more precision. Samples of blood and body fluids, as well as accurate clinical data are crucial to bring these advances to individual patients. Despite the importance of sampling, automating patient sampling and data collection is not widely practiced. Even in the most sophisticated clinical trials, data is still obtained manually and samples are still collected by hand. Collection methods can vary from hospital to hospital and the lack of standardized methods invites errors. Worldwide costs for the collection and storage of clinical specimens are in the hundreds of millions of dollars. More importantly, the study of diseases and biomarkers are not advancing due to the lack of availability of quality samples.

The expense of manually collecting patient data and samples for clinical trials is not trivial. Research coordinators, often nurses, must obtain or oversee the obtaining of samples, perhaps multiple times per day. A data collector must search the medical record and transcribe the data, often interfacing with multiple computer systems. The cost and labor requirements for clinical trials are confining them to the larger hospitals and academic centers, or sending them overseas where costs are lower. This has led to a gradual erosion of the credibility of clinical trial results due to their questionable applicability to most community-based clinicians, who have different local practices and different patient populations. There is a general lack of cost effective tools for conducting patient research in community hospitals. Approximately 4500 out of 5000 hospitals in the U.S. are community hospitals and that is where most patients receive health care.

The vast majority of clinical samples taken in clinical trials and medical practice are blood and urine samples. These come with a significant time commitment. Blood must be drawn either by sticking a vein with a needle, which can be very difficult in some patients, or by removing it from an intravascular catheter, using an appropriate sterile technique. Urine samples are often removed from a urine collection system, again using a sterile technique. There is a practical limit to how often these samples can be taken. Furthermore, there is a growing interest in obtaining other body fluids such as interstitial fluid from under the skin, from the brain, wounds, and transplanted organs, as well as cerebrospinal fluid, pleural fluid, ascites, and other body fluids. The technique of microdialysis, which can take continuous microliter sized samples from all of these sites, remains largely a research tool. The inconvenience of bulky fraction collectors, manually switching out of tubes, and problems with evaporation during microdialysis have all limited it largely to the realm of research.

Due to these limitations, current patient data collection and sampling methods are time consuming, expensive, and limited in how often and what they can sample. It would therefore be advantageous to develop an automated sampling and data collection system that is capable of sampling multiple body sites and collecting high volumes of data.

BRIEF SUMMARY OF THE INVENTION

One object of the present invention is to provide a system and method for improving the process of collecting and storing samples in a clinical setting. More particularly, it is an object of the present invention to allow the autonomous collection and storage of a series of specimen samples, such as blood, plasma, urine, or other body fluids, drawn from a patient undergoing treatment. The samples are drawn over a period of time that can be as long as days to weeks. Data about the samples can be stored with other relevant patient data for later use. Collected samples may be banked for later analysis, dispensed for immediate analysis, or analyzed inline. In this respect, the invention is a technology platform that can be incorporated with other analytic techniques, including real-time multi-modality and biomarker sensors.

Sample collection is accomplished by withdrawing a small amount of fluid from the patient into microfluidic or capillary tubing. The specimen can be withdrawn directly from the patient, siphoned from an existing reservoir or conduit containing the sample, such as a catheter, or obtained by microdialysis. A pump, for example a roller pump, moves the sample through the tubing. The tubing further serves as a closed collection system and multiple samples can be collected and stored as part of one continuous process. That is, a first sample remains in the tubing when a second sample is obtained and so forth. Traditional sampling techniques, on the other hand, use separate containers for each sample. Moreover, a nurse or lab technician is required to initiate the withdrawal for each sample.

To prevent mixing or contamination between multiple samples, an immiscible spacer fluid is injected into the tubing to separate the samples. If the samples will not be analyzed for a period of time after withdrawal, an integrated cooling mechanism preserves the batch of samples until they are retrieved for testing.

A sensor capable of distinguishing between a specimen sample and the spacer fluid within the tubing is provided to monitor the position of the samples. The sensor can provide additional detail about the system and the sampled fluid, such as flow rate, specimen volume, or other usable data. The data provided by the sensor and other system data, such as the time when the sample is withdrawn, are logged by a microcontroller in communication with the sensor. The microcontroller is in further communication with the pump to control the withdrawal schedule, volume, and spacing of the specimens. The microcontroller is also in communication with the patient Electronic Medical Record (EMR) and other data sources such as bedside monitors or other databases, in order to download and store relevant patient data.

DETAILED DESCRIPTION OF THE INVENTION

Figure 1:
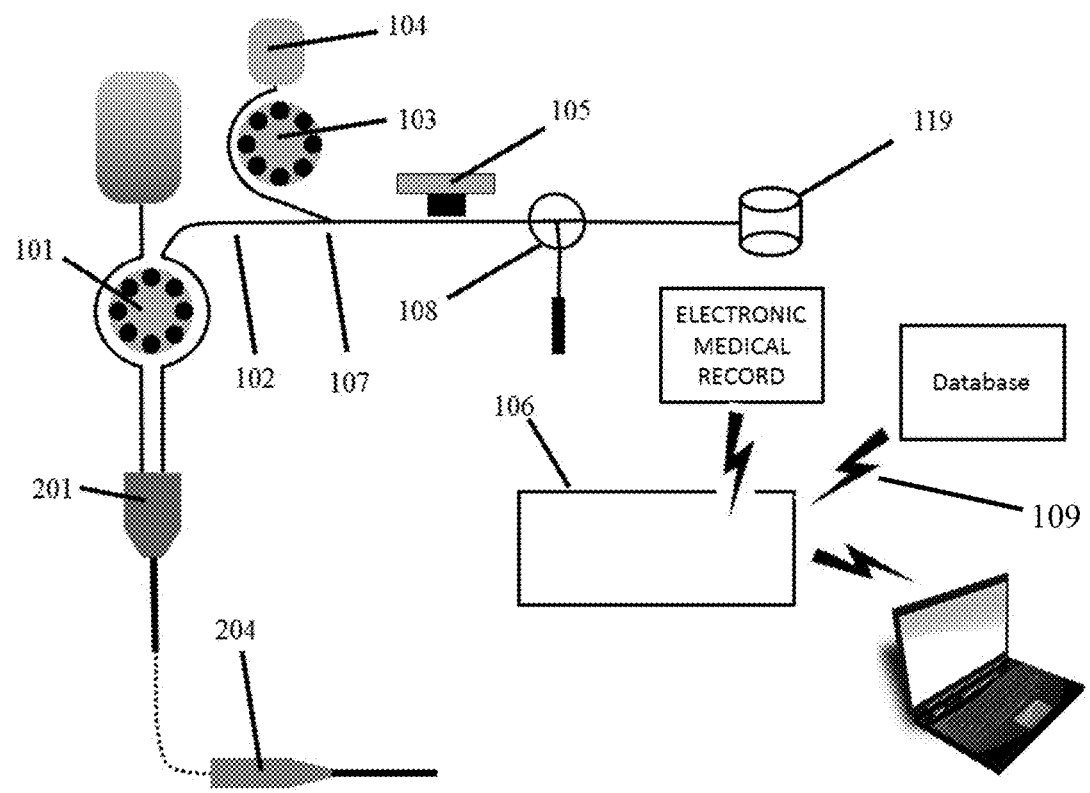
FIG. 1 depicts the system according to one embodiment of the present invention.

As shown in FIG. 1, the data sampling and banking system comprises a pump 101 for moving a sample through tubing 102, a separate, secondary pump 103 for injecting a spacer fluid 104 through a junction 107, such as a Y-connector or valve, into the tubing 102 containing the sample, a sensor 105 for identifying samples within the tubing 102, a microprocessor 106 for operating the sample pump 101 and secondary pump 103, for receiving, storing, and transmitting data from one or more sensors 105, and for retrieving information from the Electronic Medical Record (EMR) or other data sources, and a valve 108 with a side port inline with the tubing 102 for immediate dispensing of samples if desired.

In the preferred embodiment, the tubing 102 is microfluidic tubing having an inner diameter of about 0.66 millimeters. However, an inner diameter from about one nanometer to several thousand micrometers is acceptable. The upper size limit is dependent on maintaining sample separation and varies depending on the physical characteristics of the sample fluid and the tubing 102. Beyond the upper limit, mixing between the sample and the spacer can occur as the boundary between the two becomes degraded. Tubing 102 having a diameter on the smaller end of the range has certain advantages for the collection of precious body fluids. For example, if the sample to be collected is blood, using smaller tubing is beneficial to minimize the amount of red bloods cells, iron, and hemoglobin removed from the patient.

The tubing 102 can be constructed from a variety of materials typically used for microfluidic tubing, such as polyetheretherketone, polytetrafluoroethylene (Teflon®), fluorinated ethylene-propylene, ethylene tetrafluoroethylene, and polypropylene. Moreover, the tubing material can be hydrophobic or hydrophilic. Hydrophobic materials are beneficial to prevent the sample from adhering to the tubing wall. Although, some proteins can bind to the surface of hydrophobic materials. In situations where proteins are a component of interest in the sample, a hydrophilic material could be a better choice for tubing material. Alternatively, a hydrophilic treatment can be imparted on the interior wall of hydrophobic tubing 102. Treatments range from altering the surface chemistry with a coating, patterning the surface to alter the wettability, or applying other techniques known in the art.

While many different tubing materials are suitable, in the preferred embodiment, the tubing is constructed of polytetrafluoroethylene as it has an affinity when used with liquid fluorocarbon as the spacer fluid 104. The affinity between the two materials results in a resistance to deformation of the boundary between the sample and the spacer fluid 104. Moreover, the strong attraction between the wall of the tubing 102 and the fluorocarbon spacer fluid 104 can result in a wiping action that inhibits a film from one sample remaining on the tubing wall and mixing with the next sample as it travels along the tubing 102.

The sample pump 101 can be a roller pump, a peristaltic pump, or any other type of pump typically used with microfluidic tubing. Pumps often used in medical settings, such as peristaltic pumps, act on the tubing and do not contact the fluid contained within the tubing. This function is important since the relatively expensive pump can be reused for multiple patients, while only the relatively inexpensive tubing is disposed. In the preferred embodiment, the pump 101 is equipped with a stepper motor that is capable of drawing fluid into the tubing 102 in discrete amounts. With the use of a stepper motor, each sample obtained by the system will have the same volume, which can be important for laboratory analysis. In this example and other embodiments, microcontroller 106 controls the operation and timing of pump 101.

Figure 4:
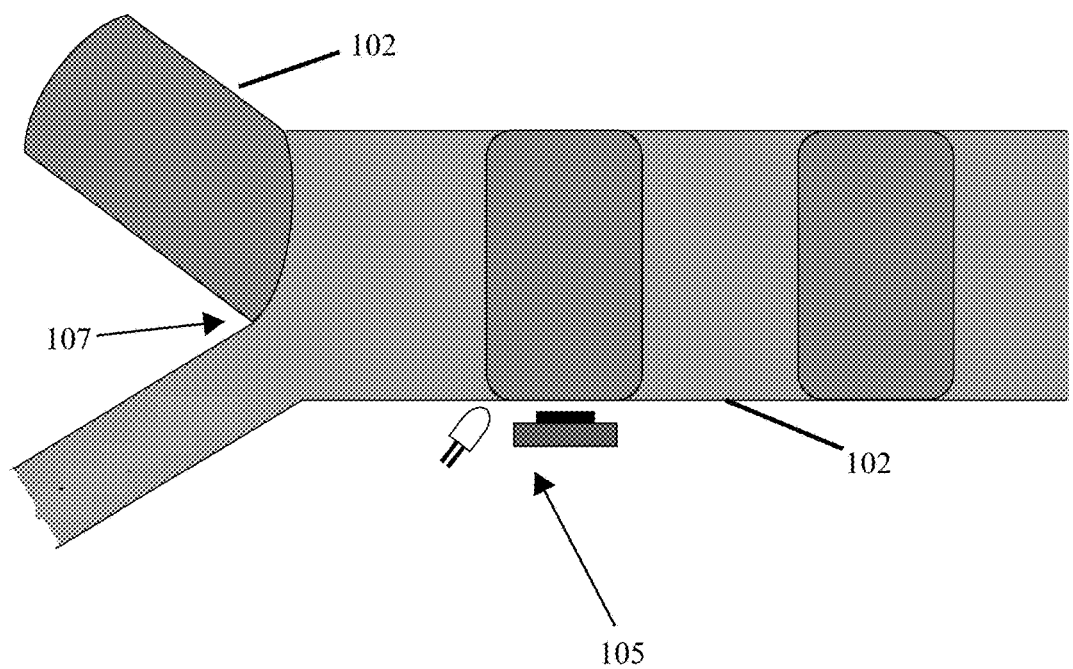
FIG. 4 is a schematic showing tubing containing samples separated by spacer fluid plugs and an imaging sensor for identifying samples.

A secondary pump 103, such as a peristaltic pump, syringe pump, or pump similar to those suitable for sample pump 101, dispenses an immiscible spacer fluid 104 into the tubing 102 carrying the sample to isolate sequential samples. That is, spacer fluid 104 is injected after each sample to provide separation from a subsequent sample. A separate line of tubing transports the spacer fluid 104 from a reservoir to the main tubing 102 carrying the sample. A connection, valve, or other suitable connector 107 is provided to splice the tubing 102 with the spacer fluid 104 supply line, allowing the spacer fluid 104 to be interposed between samples in the sample tubing 102. FIG. 4 shows the intersection of the spacer fluid 104 line and the sample tubing 102. Upstream in the spacer fluid line is pure spacer fluid 104. Likewise, upstream in the sample tubing 102 is pure sample. After the junction, discrete sections of spacer fluid 104 are interspersed between individual samples. Microcontroller 106 controls the operation and timing of secondary pump 103 to ensure proper coordination with the sample pump 101.

Figure 3:
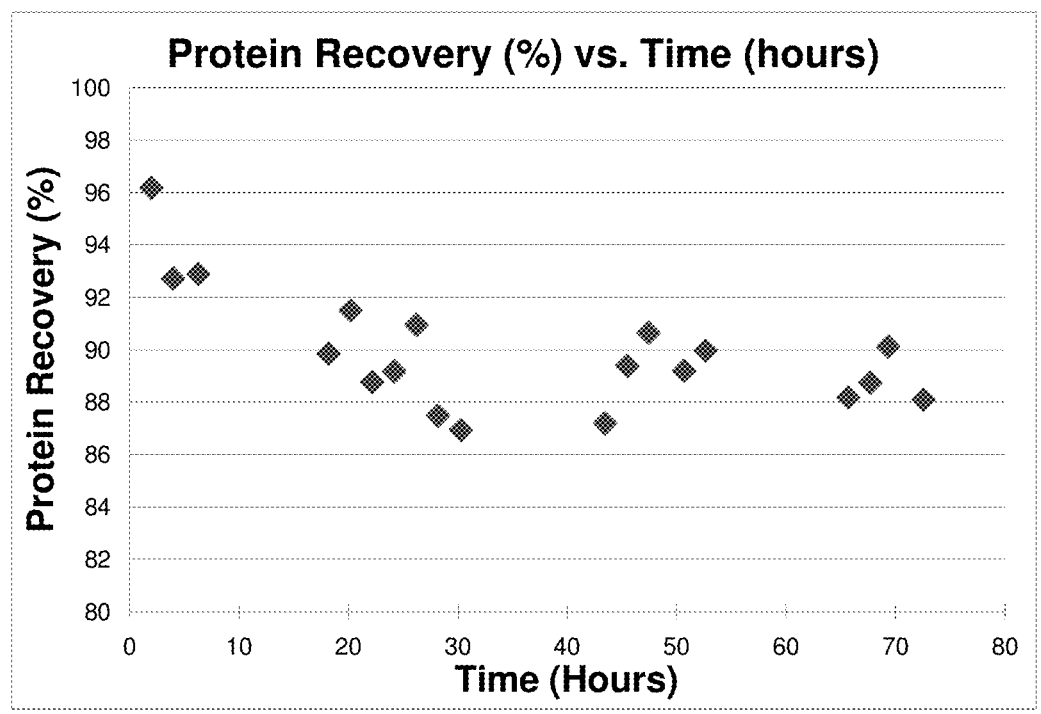
FIG. 3 is a graphical representation of the detection of a protein in human blood during a sample collection period of three days using the system and method of the present invention.

Depending on the operation of the primary pump 101 and the intending spacing of samples, the operation of the secondary pump 103 will vary. For example, if urine is being sampled from a urinary catheter on a continuous basis, the secondary pump may inject the spacer fluid 104 intermittently—such as every twenty minutes—to create discrete samples corresponding to a known time. FIG. 3, for example, shows protein recovery in a group of samples as a function of time. That is, the first sample represents the concentration of protein during the first hour; the second sample represents the concentration at the second hour, and so forth. To accomplish the separation for a continuous sampling, microcontroller 106 will instruct the secondary pump 103 to inject a volume of spacer fluid 104 once every hour.

Conversely, if samples are withdrawn intermittently, the secondary pump 103 will have to synchronize injection of the spacer fluid 104 with the withdrawal of the sample. By way of example, if a sample is withdrawn every 5 minutes, the secondary pump 103 will inject a volume of spacer fluid every five minutes as well, either before or after the sample is withdrawn. In this manner, adjacent samples are separated by spacer fluid 104 regardless of whether the samples are drawn continuously or intermittently.

A wide variety of spacer fluids 104 can be utilized in the system and method of the present invention. Examples of suitable fluids include, but are not limited to, air, mineral oil, liquid fluorocarbons, hydrocarbons, nanoparticles, and others. It is critical, however, that the spacer fluid 104 be immiscible with the sample to be collected. As previously mentioned, liquid fluorocarbons (such as 3M™ Fluorinert™ products) are used in the preferred embodiment due to favorable physical properties, including its low miscibility with water, water-based fluids, and most organic solvents. The low miscibility means that the boundary between the spacer fluid 104 and the sample will remain intact without dilution or mixing between the two as they are moved along the tubing 102. Moreover, fluorocarbon liquids interact favorably with common tubing materials, such as polytetrafluoroethylene.

The timing of injection of the spacer fluid 104 can be altered to create unique effects. For example, sequential aliquots of spacer fluid 104 can have different lengths, whereby creating a bar code like pattern that can be used to identify individual patients or samples. The code can be recognized by the sensor 105 or equipment used in the laboratory for off-site analysis. The generation of these varying patterns is controlled by the microprocessor 106.

As shown in FIG. 1, a sensor 105 is provided to identify individual samples. Location of the sensor 105 can occur anywhere along the tubing 102 downstream from the junction with the spacer fluid 104 line. The sensor 105 can be a variety of devices known in the art that are capable of distinguishing between a section of spacer fluid 104 and a section of sample. By way of example, a photosensor, such as a CMOS image sensor, can be used to identify the sections. In this example, the spacer fluid 104 can be dyed to provide improved contrasts between the two fluids. As another example, a sensor 105 that measures conductance can be used if the spacer fluid is a dielectric, which both air and fluorocarbon liquids are. If a sensor 105 that measures conductance is used, the spacer fluid 104 should be a dielectric since most body fluids are highly conductive.

Additional sensors can be incorporated into the system depending on the needs of a user. For example, a bubble sensor (which is known in the art) can be placed on the sample tubing 102 to detect the presence of air in the line. If air is present, the microcontroller 106 can send a signal to a nurse to inspect the system or it can temporarily cease operation of the sample pump 101 and the secondary pump 103 until the condition is corrected.

The data obtained by sensor 105 is communicated to the microcontroller 106, which can use the sensor information to time stamp particular samples, confirm discretization is occurring, calculate flowrate and sample volume, or confirm that the pumps are operating properly. For example, if the diameter of the tubing 102 and the revolution or pulse speed of the stepper motor are known, then the volume of a sample can be calculated by microcontroller 106. In turn, the sensor 105 can indicate the time a sample takes to pass the sensor 105, giving the volumetric flowrate. In the preferred embodiment, the microcontroller 106 is a single-board computer having a processor, memory, clock, input/output bus, data storage, and wireless connectivity.

In addition, the microcontroller 106 has the capability to transfer sample and clinical data to remove devices through a communications interface 109. For example, EMR systems have plug-ins that permit automated data acquisition from ancillary devices, which would include the system of the present invention. The microcontroller 106 can also provide the following functionality: wirelessly transmit data to allow for remote monitoring of system status; perform clinical data acquisition from the EMR; send alarms to clinicians when desirable variable limits are exceeded, such as high heart rate, low blood pressure, and the like; provide a user interface for setting flow rates and to select between sample storage and immediate dispensing.

With respect to data acquisition, the microcontroller 106 has a wireless capability to gather patient data from the Electronic Medical Record. The device, for example, could use the IEEE 11073 standard on the device side and the HL7 interface on the EMR side to obtain patient data that is de-identified and matched to the samples by a code number. In addition to acquiring data from the sensor 105 and an EMR system, the microcontroller could also accept data input from other sources.

The microcontroller 106 further has the capability to set the flow rates of the perfusate and dialysate within the push-pull pump connected to a microdialysis probe; the capability to monitor tracer concentrations measured in the perfusate; and the capability to control the dispensing of the collected samples into vials for later analysis or to control the dispensing of collected samples into a side port 108 for immediate analysis or to waste disposal.

Figure 5:
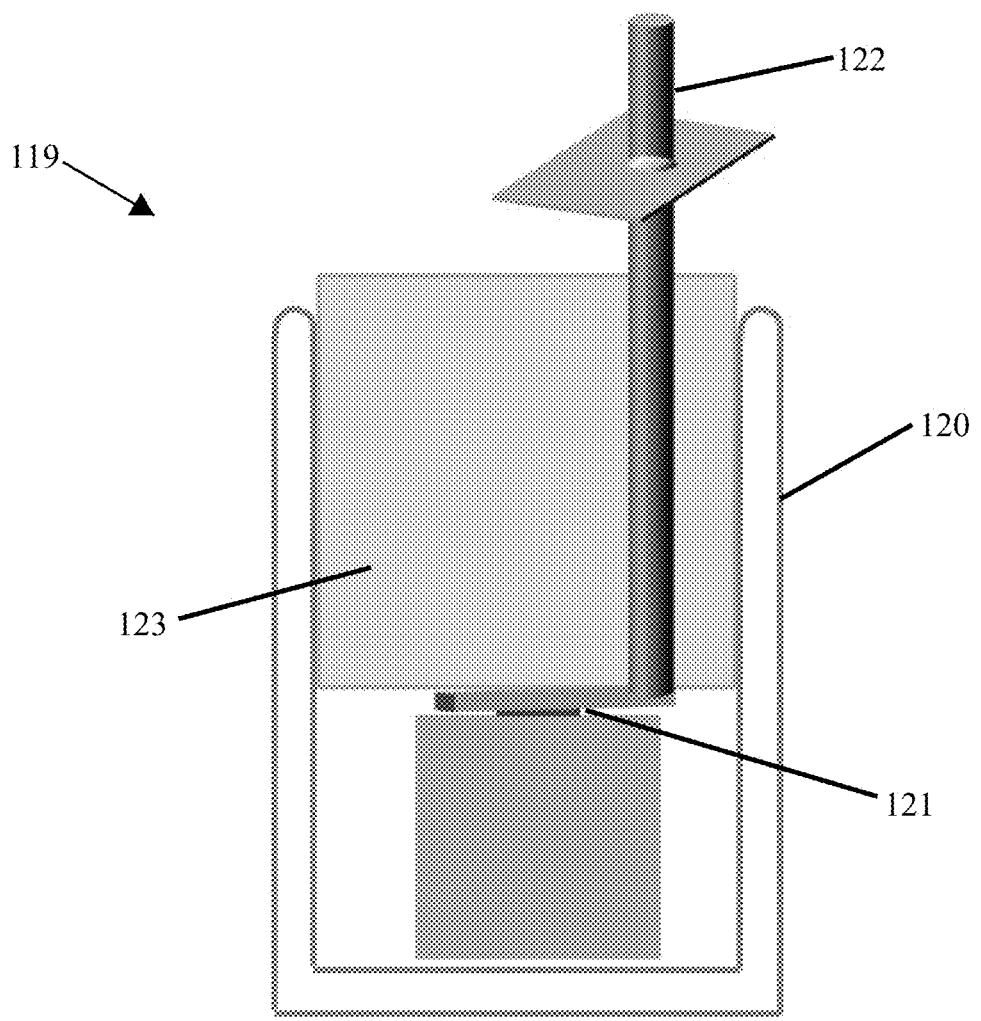
FIG. 5 depicts an optional cooled storage container for the samples.

In situations where the samples will not be used immediately, a cooling mechanism 119 is provided to preserve the samples stored in the tubing 102. As shown in FIG. 5, the cooling mechanism 119 comprises an insulated storage vessel 120, a thermoelectric cooler 121 (also known as a Peltier cooler) positioned within the storage vessel 120, and a heat pipe 122. The warm side of the thermoelectric cooler is thermally affixed to the heat pipe 122, which passes through a layer of insulating material 123 covering an opening in the storage vessel 120. With the use of a heat pipe 122, excess heat generated by the thermoelectric cooler 121 is transferred to the outside of the storage vessel 120. Alternatively, the thermoelectric cooler 121 can be placed on the exterior of the storage vessel 120, with the cool side thermally connnected to the interior.

When a cooling mechanism 119 is used, the tubing 102 is coiled around the interior of the storage vessel 120, which is a vacuum-insulated container in the preferred embodiment. In one emdodiment, the tubing 102 is coiled around a cylindrical metal heat sink, much like thread on a spool, within the vessel 120, wherein the heat sink is thermally connected to the thermoelectric cooler. The thermoelectric cooler 121 is sized appropriately to maintain the interior of the storage vessel 120 at a temperature of around 1-3 degrees Celsius, for example, to prevent the samples stored in the vessel 120 from degrading. As an alternative method of preserving the samples, the spacer fluid 104 can be co-delivered, either simultaneously or sequentially, with an aqueous solution containing protease inhibitors that include metal chelators, enzyme inhibitors, or other preservatives. This same technique can be used to supply other dissolved components to the sample, for example to create reactions that will identify constituents such as urea or other molecules within the sample. Similarly, antibodies or nucleic acid probes capable of detecting targets within the sample could be added, allowing inline or offline detection of organic molecules, peptides, DNA, or RNA targets.

The basic components of the system of the present invention have thus far been described. In addition to these components, the system can further comprise various sampling devices for introducing a sample into tubing 102. In one embodiment, an open end of tubing 102 collects samples directly from free-flowing fluids such as ascites, pleural effusion, and urine. Negative pressure in the sampling tubing 102 is produced by the sample pump 101. Alternatively, for urine sampling, the tubing 102 can attach to the end of a standard urinary catheter. As another example, a tubular conduit sampling breath condensate from exhaled air can be integrated into the system. Microdialysis units are an additional component intended to be used with the system.

Figures 2A, 2B:
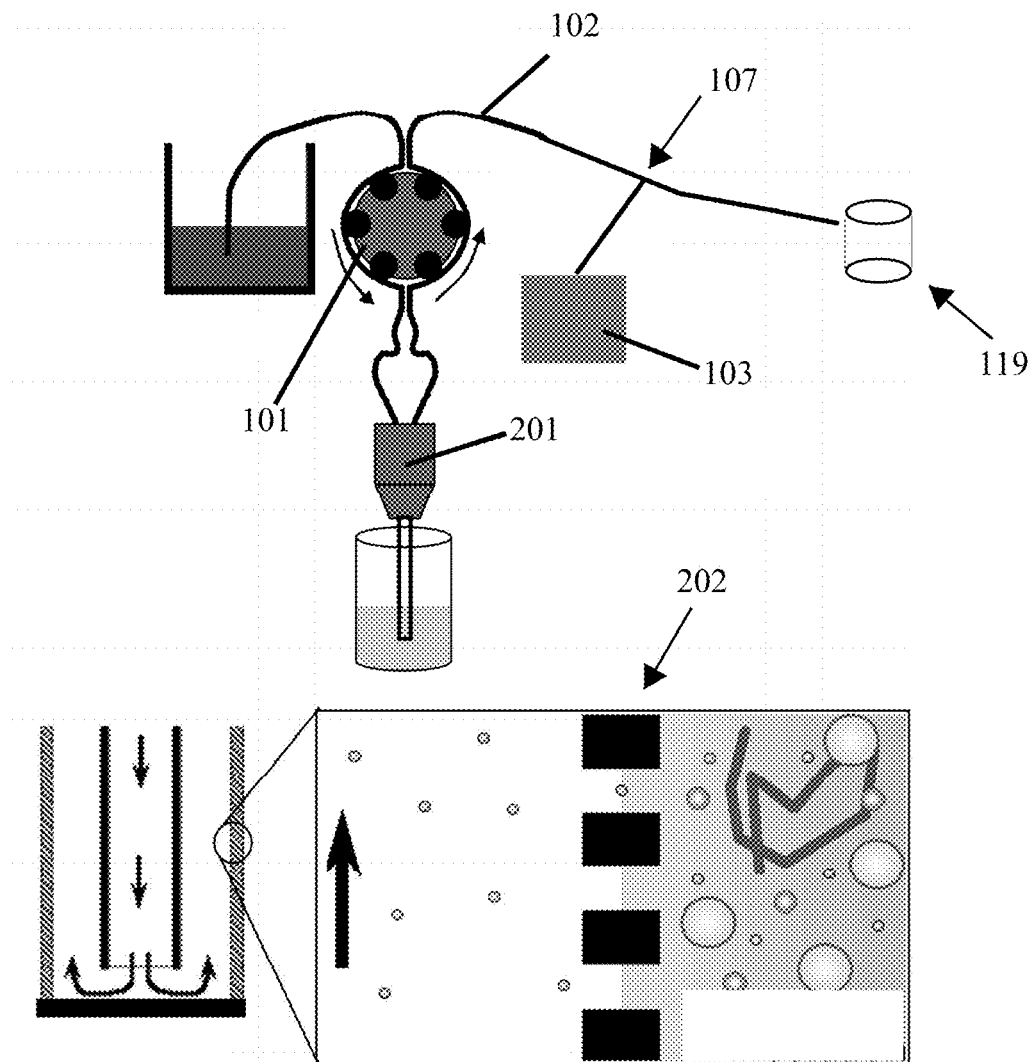
FIG. 2A depicts a microdialysis unit as the sampling device used with the system according to one embodiment of the present invention.
FIG. 2B is a close-up view of the microdialysis probe showing fluid flow across a membrane.

Referring again to FIG. 1, this particular embodiment of the system incorporates an intravenous, push-pull microdialysis probe 201, which can be inserted into a peripheral vein catheter 204 and can remain inserted for several days. Microdialysis is one of the few sampling techniques that permit continuous monitoring of a patient. The intravenous microdialysis probe 201 includes a semipermeable membrane 202, as seen in FIGS. 2A and 2B, which allows the transfer of certain molecules from the surrounding body fluid into the interior of the probe 201. A carrier fluid, known as a perfusate, is pumped (or pushed) into the inlet of probe 201 to enable the transfer. Stated differently, when the perfusate is circulated through the microdialysis probe 201, analyte molecules from the surrounding environment are exchanged across the semipermeable membrane 202 into the microdialysis probe 201, thereby producing a dialysate.

The same pump 101 pulls the dialysate in the opposite direction of the perfusate. As a person having skill in the art will appreciate, operating both the pushing and pulling operations off the same pump synchronizes the push and pull functions and prevents a pressure or flow differential between the two.

In alternative embodiments, a perfusate containing real-time detectable tracer molecules is used. When the perfusate is pumped into the microdialysis probe, a portion of the tracer molecules are exchanged across the semipermeable membrane into the surrounding environment. The tracer molecules can be detected using optical, electrical, or chemical means.

As an example of a method of collecting and storing a sample using a microdialysis probe, a typical experiment is described. The description of this method is meant to be illustrative, but should not be read to limit the method to this particular set-up. The first step requires obtaining a large molecular weight cut-off (MWCO) microdialysis probe. The probe is then placed into a venous catheter in a patient. The microdialysis probe, having a molecular weight cut-off of 3000 kD, will remain in place for over 72 hours. A peristaltic pump pushes perfusate into the probe and pulls the dialysate from the probe. The dialysate samples are collected with Teflon® tubing (having an inner diameter of 0.66 mm) to prevent evaporation. The pump is set to 0.1 RPM, provided a constant flow rate of 0.16 microliters/min throughout the experiment. The perfusate is provided with pH 7.4 phosphate buffered saline with ionic strength adjusted to 154 milliosmols using sodium chloride, closely approximating plasma. The secondary pump 103 injects the Flourinert™ FC-75 liquid fluorocarbon to separate samples. The samples are then collected in a vacuum-insulated container, kept below 3 degrees Celsius, for the duration of the trial. At the end of the trial, the entire container, including the tubing containing the samples and spacer fluid, is shipped to a diagnostic laboratory for testing.

The invention disclosed herein is not intended to be limited to the details disclosed. Rather, various modifications may be made in the details without departing from the invention. In addition, while the disclosure has been described in detail and with reference to specific embodiments, the embodiments are examples only. Thus, it is intended that the present disclosure cover the modifications and variations of this disclosure provided they come within the scope of the appended claims and their equivalents.

What is claimed is:

1. A patient data and sample collection and banking system comprising:
  a tube capable of transporting a sample;
  a first pump coupled to the tube, wherein the first pump moves the sample through the tube;
  a spacer fluid;
  a second pump in fluid communication with the spacer fluid and connected to the tube, wherein the second pump is capable of injecting the spacer fluid into the tube;
  a sensor capable of differentiating between the sample and the spacer fluid contained within the tube, wherein the sensor generates a data signal;
  a microcontroller electrically connected to each of the sensor, the first pump, and the second pump, wherein the microcontroller sends control signals to the first pump and the second pump, causing the second pump to interpose the spacer fluid between the sample and an adjacent subsequent sample; and
  a communications interface connecting the microcontroller to a database, wherein the microcontroller is capable of receiving and transmitting data through the communications interface.

2. The system of claim 1, further comprising:
  a storage vessel, wherein a portion of the tube is contained within an interior volume of the storage vessel; and
  a cooling device that cools the interior volume of the storage vessel.

3. The system of claim 2, wherein the cooling device is a thermoelectric cooler.

4. The system of claim 1, wherein the database is an electronic medical record system.

5. The system of claim 1, wherein the communications interface is wireless.

6. The system of claim 1, wherein the microcontroller receives the data signal from the sensor.

7. The system of claim 1, wherein the spacer fluid is a fluorocarbon.

8. The system of claim 1, wherein the tube is hydrophobic.

9. The system of claim 1, wherein the tube is hydrophilic.

10. The system of claim 1, wherein the microcontroller further comprises a single-board computer.

11. The system of claim 1, wherein the microcontroller is electrically connected to each of the sensor, the first pump, and the second pump by a wireless connection.

12. A method of collecting patient data and collecting and banking patient samples, the method comprising:
  drawing a sample into a tube;
  moving the sample along a portion of the length of the tube through the use of a pump;
  injecting a spacer fluid into the tube containing the sample to create sequential samples comprising a first sample and a second sample;
  wherein the spacer fluid is interposed between the first sample and the second sample to create discrete sections of sample and spacer fluid along the tube;
  sensing at least one of the first sample, the second sample, and the spacer fluid at a point along the tube;
  providing a microcontroller in communication with the sensor and the pump;
  sending a control signal from the microcontroller to the pump;
  receiving data in the microcontroller from the sensor, wherein the data comprises an identification of at least one of the first sample and the second sample, wherein each identified sample contains a time stamp; and
  receiving and storing additional data in the microcontroller from at least one of a database and a data source.

13. The method of claim 12, further comprising:
drawing a plurality of samples into the tube, wherein each of the plurality of samples is separated by an aliquot of the spacer fluid.

14. The method of claim 13, further comprising:
spacing the plurality of samples to form a code used for the identification of the samples.

15. The method of claim 12, wherein:
the additional data comprises data from an electronic medical records system.

16. A sample collection and banking system comprising:
a sampling device for collecting a sample;
a tube in fluid communication with the sampling device;
a pump coupled to the tube, wherein the pump moves the sample through the tube;
a spacer fluid, wherein the spacer fluid is injected into the tube containing the sample;
a connector coupled to the tube to allow the spacer fluid to be interposed between portions of the sample in the tube;
a sensor capable of differentiating between the sample and the spacer fluid contained within the tube;
a microcontroller electrically connected to the sensor and the pump, wherein the microcontroller sends a control signal to the pump and receives data from the sensor; and
a communications interface connecting the microcontroller to a database, wherein the microcontroller is capable of receiving and transmitting data through the communications interface.

17. The system of claim 16, wherein the sampling device is a microdialysis probe.

18. The system of claim 16, wherein the sampling device is connected to at least one of a urinary, pleural, spinal, or intra-abdominal catheter.

19. The system of claim 16, further comprising:
a storage vessel, wherein a portion of the tube is contained within an interior volume of the storage vessel; and
a cooling circuit that cools the interior volume of the storage vessel.

20. The system of claim 19, wherein the cooling circuit is a thermoelectric cooler.

21. The system of claim 16, wherein the database is an electronic medical record system.

22. The system of claim 16, wherein the communications interface is wireless.

* * * * *